United States Patent
Fuchs et al.

(10) Patent No.: US 6,663,844 B1
(45) Date of Patent: Dec. 16, 2003

(54) PYROGENIC TITANIUM DIOXIDE

(75) Inventors: Eberhard Fuchs, Frankenthal (DE); Klemens Flick, Herxheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/486,488

(22) PCT Filed: Aug. 24, 1998

(86) PCT No.: PCT/EP98/05356

§ 371 (c)(1),
(2), (4) Date: Feb. 29, 2000

(87) PCT Pub. No.: WO99/11615

PCT Pub. Date: Mar. 11, 1999

(30) Foreign Application Priority Data

Sep. 3, 1997 (DE) .......................................... 197 38 462

(51) Int. Cl.⁷ .............................................. C01G 23/07
(52) U.S. Cl. ....................................................... 423/613
(58) Field of Search .......................... 540/539; 423/610, 423/611, 612, 613; 546/243; 548/553; 502/439; 264/623; 501/127

(56) References Cited

U.S. PATENT DOCUMENTS

| | | | |
|---|---|---|---|
| 4,021,454 A | * | 5/1977 | Wulff et al. .......... 260/348.5 L |
| 4,061,596 A | | 12/1977 | Matsushita et al. |
| 5,276,201 A | * | 1/1994 | Haas et al. .................. 568/491 |
| 5,502,185 A | * | 3/1996 | Fuchs et al. ................. 540/538 |
| 5,646,277 A | | 7/1997 | Fuchs et al. |
| 5,723,603 A | * | 3/1998 | Gilbert et al. .............. 540/539 |
| 5,739,324 A | | 4/1998 | Fuchs et al. |

FOREIGN PATENT DOCUMENTS

| | | |
|---|---|---|
| DE | 25 54 198 | 8/1976 |
| DE | 32 17 751 | 11/1983 |
| DE | 43 39 648 | 5/1995 |

* cited by examiner

*Primary Examiner*—Stanley S. Silverman
*Assistant Examiner*—Edward M. Johnson
(74) *Attorney, Agent, or Firm*—Keil & Weinkauf

(57) ABSTRACT

Shaped materials useful as catalyst for preparing cyclic lactams by reacting aminocarbonitriles with water in the liquid phase in a fixed bed reactor and which have no soluble constituents under the reaction conditions, comprising pyrogenic titanium dioxide as essential constituent, these compositions being obtainable by shaping the pyrogenic titanium dioxide into shaped articles and, before or after the shaping, treating the pyrogenic titanium dioxide with from 0.1 to 30% by weight, based on the pyrogenic titanium dioxide, of an acid in which pyrogenic titanium dioxide is sparingly soluble.

2 Claims, No Drawings

PYROGENIC TITANIUM DIOXIDE

SPECIFICATION

The present invention relates to shaped materials useful as catalyst for preparing cyclic lactams by reacting aminocarbonitriles with water, said shaped materials essentially comprising titanium dioxide.

DE-B 25 54 198 discloses shaped titanium dioxide articles obtained by shaping titanium dioxide and calcining the shaped articles at 300 to 800° C., the titanium dioxide being prepared by hydrolysis of a titanium salt and being treated, before or after said shaping, with from 0.01 to 50% by weight, based on titanium dioxide, of a mineral acid or of an organic acid.

However, such shaped articles have the disadvantage that titanium dioxide prepared by hydrolysis is insufficiently pure for catalytic purposes. This leads to losses in yield and selectivity in reactions where such shaped articles are used as catalyst.

DE-C 32 17 751 discloses moldings useful as catalyst which are up to 99% by weight pyrogenic titanium dioxide, have an $SiO_2$ content of from 0 to 1% by weight, accessible pore volume of 45–55% of the volume of the molding and a breaking strength of not less than 1.630 N. Such moldings have the disadvantage that their preparation requires the use of a molding aid, sieving of the mixture and conversion of the sieved mixture into a flowable powder in order that tablets may be produced with the aid of a tableting press. Pyrogenic titanium dixoide is produced by high temperature hydrolysis of a vaporizable titanium compound, normally titanium tetrachloride, in a detonating gas (mixture of hydrogen and oxygen gas) flame.

It is an object of the present invention to provide shaped materials comprising titanium dioxide as essential constituent which are useful as catalyst, which do not have the disadvantages mentioned and which can be produced in a technically simple and economical manner.

We have found that this object is achieved by shaped materials which are useful as catalyst and which have no soluble constituents under the reaction conditions, comprising pyrogenic titanium dioxide as essential constituent, said shaped materials being obtainable by shaping the pyrogenic titanium dioxide into shaped articles and, before or after said shaping, treating the pyrogenic titanium dioxide with from 0.1 to 30% by weight, based on the pyrogenic titanium dioxide, of an acid in which pyrogenic titanium dioxide is sparingly soluble.

The pyrogenic titanium dioxide can be present in various modifications such as amorphous, as anatase or as rutile or phase mixtures thereof.

The aforementioned titanium dioxide can be doped with, or comprise, compounds of main groups 1 to 7, especially 2, 3 or 4, of the periodic table, alumina, such as alpha- or gamma-alumina, or tin oxide, of transition groups 1 to 7 of the periodic table, of the elements of the iron group or of the lanthanides, preferably cerium oxide, or actinides and also mixtures thereof.

If desired, these catalysts may comprise up to 50% by weight in each case of copper, tin, zinc, manganese, iron, cobalt, nickel, ruthenium, palladium, platinum, silver or rhodium.

These catalytically active oxides are preparable in a conventional manner, for example by hydrolysis of the corresponding organics, alkoxides, salts with organic or inorganic acids and subsequent heating or calcining and also pyrogenically and are generally commercially available.

According to the invention, the oxides are treated with an acid before or after shaping. Suitable acids include organic acids such as oxalic acid, propionic acid, butyric acid, maleic acid or inorganic acids such as isopolyacids, heteropolyacids, sulfuric acid or hydrochloric acid. Particularly suitable catalysts are obtainable by treatment with acetic acid, formic acid, nitric acid, especially phosphoric acid.

It is also possible to use mixtures of acids.

The treatment can be carried out continuously or batchwise in one or more stages. The individual stages can be carried out with the same acid, different acids or identical or different mixtures of acids.

Similarly, the oxides can be treated with an acid in the form mentioned before and after shaping.

Preferably, the oxides are treated with an acid before shaping.

The amount of acid used according to the invention is from 0.1 to 30%, preferably from 0.1 to 10%, especially from 0.1 to 5%, by weight, reckoned as pure acid, based on pyrogenic titanium dioxide. The acid can be mixed with a liquid diluent, such as water.

The catalysts can be prepared from the oxides without additives. It is similarly possible to add additives such as binders, for example titanium dioxide sols, salts of the oxides used, soluble titanium salt compounds, hydrolyzable titanium compounds such as titanium alkoxides or aluminum salts, such as pore-formers, for example methylcellulose, carbon fibers, fibers of organic polymers, melamine, starch powder, preferably before shaping.

The shaped articles can be present in various forms, for example as ball, tablet, cylinder, hollow cylinder, pellet, granule or strand. Such shaped articles are preparable in a conventional manner using appropriate shaping machines such as tableting machines, extruders, rotary granulators, pelletizers or combinations thereof.

The shaped material, if desired after an acid treatment, is advantageously dried, especially at from 20 to 120° C., preferably in an inert gas atmosphere or in the air, and then calcined, especially at from 400–750° C., preferably in an inert gas atmosphere or in the air.

The shaped materials can advantageously be used as catalyst for preparing cyclic lactams by reacting aminocarbonitriles with water in the liquid phase in a fixed bed reactor.

To this end, the heterogeneous catalysts can be arranged in a fixed bed. The reaction can take place in a conventional manner, for example in a downflow or preferably upflow mode, especially continuously, by bringing the reaction mixture into contact with the catalyst bed.

The starting materials used in the process of the present invention are aminocarbonitriles, preferably those of the general formula I

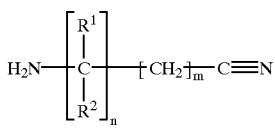

(I)

where n and m are each 0, 1, 2, 3, 4, 5, 6, 7, 8 or 9 and n+m totals at least 3, preferably at least 4.

$R^1$ and $R^2$ can in principle be substituents of any type. It is merely necessary to ensure that the desired cyclization reaction is not affected by the substituents. Preferably, $R^1$ and $R^2$ are independently $C_1$–$C_6$-alkyl or $C_5$–$C_7$-cycloalkyl or $C_6$–$C_{12}$-aryl.

Particularly preferred starting compounds are aminocarbonitriles of the general formula

where m is 3, 4, 5 or 6, especially 5. When m=5, the starting compound is 6-aminocapronitrile.

In the process of the present invention, the above-described aminocarbonitriles can be reacted with water in the liquid phase using heterogeneous catalysts to form cyclic lactams. Use of aminocarbonitriles of the formula I results in the corresponding cyclic lactams of the formula II

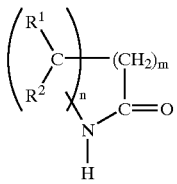

where n, m, $R^1$ and $R^2$ are each as defined above. Particularly preferred lactams are those where n is 0 and m is 4, 5 or 6, especially 5 (caprolactam being obtained in the latter case).

The reaction can be carried out in the liquid phase at generally from 140 to 320° C., preferably at from 160 to 280° C.; the pressure is generally within the range from 1 to 250 bar, preferably from 5 to 150 bar, it being necessary to ensure that the reaction mixture is predominantly liquid under the conditions employed. The residence times are generally within the range from 1 to 120, preferably from 1 to 90, and especially from 1 to 60, min. In some cases, residence times of from 1 to 10 min have proven to be completely adequate.

The amount of water used per mole of aminocarbonitrile is generally at least 0.01 mol, preferably within the range from 0.1 to 20 mol, especially within the range from 1 to 5 mol.

The aminocarbonitrile can be advantageously used in the form of a from 1 to 50% strength by weight, especially from 5 to 50% strength by weight, particularly preferably from 5 to 30% strength by weight, solution in water (in which case the solvent is also reactant) or in water/solvent mixtures. Examples of usable solvents are alkanols such as methanol, ethanol, n- and i-propanol, n-, i- and t-butanol and polyols such as diethylene glycol and tetraethylene glycol, hydrocarbons such as petroleum ether, benzene, toluene, xylene, lactams such as pyrrolidone or caprolactam, or alkyl-substituted lactams such as N-methyl-pyrrolidone, N-methylcaprolactam or N-ethylcaprolactam, and also carboxylic esters, preferably of carboxylic acids having from 1 to 8 carbon atoms. Ammonia can also be present in the reaction. Mixtures of organic solvents can also be used. Mixtures of water and alkanols in a water/alkanol weight ratio of 1-75/25-99, preferably 1-50/50-99, have been found to be particularly advantageous in some cases.

It is in principle equally possible to use the aminocarbonitriles as solvent as well as reactant.

The advantage of the process of the present invention lies in the option to operate the cyclization continuously in a simple manner with very high throughputs and high yields and selectivities and short residence times. Since the catalysts used have a long lifetime from observations to date, the result is an extremely low catalyst consumption.

EXAMPLE

Example 1

Preparation of Pyrogenic Titanium Dioxide Extrudates 8350 g of pyrogenic titanium dioxide powder having a rutile/anatase ratio of 80/20 were kneaded for 3 hours with 47 g of 85% strength formic acid and 3750 g of water and thereafter molded in the extruder into 4 mm extrudates under a molding pressure of 70 bar. The extrudates were dried at 120° C. for 16 hours and then calcined at 500° C. for 3 hours.

Analysis of extrudates:

| | | |
|---|---|---|
| Density | 989 | g/l |
| Water regain | 0.31 | ml/g |
| Cutting hardness | 25 | N |
| Surface area | 37 | m²/g |

Examples 2 to 7

Conversion of 6-aminocapronitrile into Caprolactam

A solution of 6-aminocapronitrile (ACN) in water and ethanol in the weight ratios reported in the table was passed into a 25 ml capacity heated tubular reactor (diameter 6 mm; length 800 mm) packed with catalysts 1 and 2 recited in the table, in the form of granules. The product stream leaving the reactor was analyzed by gas chromatography. The results are recited in the table as examples.

As well as caprolactam, the product stream comprises essentially ethyl ε-aminocaprylate and ε-aminocaprylamide. Both can likewise be cyclized to form caprolactam. In addition, the stream includes from 5 to 8% of caprolactam oligomer which can be cracked to form caprolactam monomer.

TABLE

| Ex. | Catalyst | ACN [% by wt.] | Water [% by wt.] | Molar ratio ACN/H$_2$O [%] | Ethanol [% by wt.] | Temp. [° C.] | Residence time [min] | ACN conversion [%] | Capro selectivity [%] |
|---|---|---|---|---|---|---|---|---|---|
| 2 | 1 | 10 | 3.2 | 2 | 86.8 | 230 | 22 | 99 | 88 |
| 3 | 1 | 10 | 3.2 | 2 | 86.8 | 230 | 9 | 99 | 92 |
| 4 | 1 | 10 | 3.2 | 2 | 86.8 | 230 | 5 | 96 | 90 |
| 5 | 2 | 10 | 3.2 | 2 | 86.8 | 230 | 20 | 100 | 91 |
| 6 | 2 | 10 | 3.2 | 2 | 86.8 | 230 | 8 | 96 | 92 |
| 7 | 2 | 10 | 3.2 | 2 | 86.8 | 230 | 5 | 87 | 90 |

Catalysts 1 and 2 were prepared similarly to catalyst example 1:

Catalyst 1: Pyrogenic titanium dioxide extruded with 3% of phosphoric acid as 4 mm extrudates and then ground to granules 1.6–2.0 mm in size Catalyst 2: Pyrogenic titanium dioxide extruded with 0.5% of formic acid as 4 mm extrudates and then ground to granules 1.6–2.0 mm in size

We claim:

1. Shaped materials, comprising pyrogenic titanium dioxide as essential constituent, said shaped materials being obtainable by shaping the pyrogenic titanium dioxide into shaped articles and, before or after said shaping, treating the pyrogenic titanium dioxide with from 0.1 to 30% by weight, based on the pyrogenic titanium dioxide, of nitric acid, acetic acid or formic acid.

2. Shaped materials as claimed in claim 1, further comprising aluminum oxide, tin oxide, cerium oxide or mixtures thereof.

* * * * *